(12) United States Patent
Sperling

(10) Patent No.: US 11,406,503 B2
(45) Date of Patent: Aug. 9, 2022

(54) METHOD FOR OPTIMIZATION OF JOINT ARTHROPLASTY COMPONENT DESIGN

(71) Applicant: Mayo Foundation for Medical Education and Research, Rochester, MN (US)

(72) Inventor: John W. Sperling, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 38 days.

(21) Appl. No.: 16/591,930

(22) Filed: Oct. 3, 2019

(65) Prior Publication Data

US 2020/0054456 A1 Feb. 20, 2020

Related U.S. Application Data

(60) Division of application No. 15/429,037, filed on Feb. 9, 2017, now Pat. No. 10,463,497, which is a continuation of application No. 15/063,021, filed on Mar. 7, 2016, now abandoned, which is a continuation of application No. 13/818,738, filed as
(Continued)

(51) Int. Cl.
*A61F 2/30* (2006.01)
*A61F 2/40* (2006.01)
*A61F 2/46* (2006.01)
*B23P 11/00* (2006.01)

(52) U.S. Cl.
CPC ............ *A61F 2/30942* (2013.01); *A61F 2/40* (2013.01); *A61F 2/4081* (2013.01); *B23P 11/00* (2013.01); *A61F 2/4657* (2013.01); *A61F 2002/30943* (2013.01); *A61F 2002/30948* (2013.01); *A61F 2002/4663* (2013.01); *Y10T 29/49* (2015.01)

(58) Field of Classification Search
CPC .................. A61F 2/30942; A61F 2/40; A61F 2002/30948; A61F 2/4081
See application file for complete search history.

(56) References Cited

U.S. PATENT DOCUMENTS

| | | | |
|---|---|---|---|
| 5,030,237 A * | 7/1991 | Sorbie | A61F 2/3804 623/20.11 |
| 6,364,910 B1 | 4/2002 | Shultz | |
| 6,514,287 B2 | 2/2003 | Ondrla et al. | |

(Continued)

FOREIGN PATENT DOCUMENTS

| | | |
|---|---|---|
| WO | 2005082291 A1 | 9/2005 |
| WO | 2006058057 A2 | 6/2006 |

(Continued)

OTHER PUBLICATIONS

Boileau, et al., The Three-Dimensional Geometry of the Proximal Humerus, Journal of Bone and Joint Surgery (Br), 1997, 79-B:857-865.
(Continued)

*Primary Examiner* — Jacob J Cigna
*Assistant Examiner* — Michael W Hotchkiss
(74) *Attorney, Agent, or Firm* — Quarles & Brady LLP

(57) ABSTRACT

Methods and devices are disclosed for the optimization of shoulder arthroplasty component design through the use of computed tomography scan data from arthritic shoulders.

9 Claims, 2 Drawing Sheets

Related U.S. Application Data application No. PCT/US2011/049686 on Aug. 30, 2011, now Pat. No. 9,278,413.

(60) Provisional application No. 61/379,634, filed on Sep. 2, 2010, provisional application No. 61/379,222, filed on Sep. 1, 2010.

(56) References Cited

U.S. PATENT DOCUMENTS

| | | | |
|---|---|---|---|
| 6,699,289 B2 | 3/2004 | Iannotti et al. | |
| 6,736,851 B2* | 5/2004 | Maroney | A61F 2/4014 623/19.12 |
| 6,944,518 B2* | 9/2005 | Roose | G16H 50/50 700/117 |
| 7,618,451 B2 | 11/2009 | Berez et al. | |
| 7,892,287 B2 | 2/2011 | Deffenbaugh | |
| 8,155,264 B2 | 4/2012 | Lessick | |
| 8,480,750 B2 | 7/2013 | Long | |
| 8,556,980 B2 | 10/2013 | Deffenbaugh | |
| 8,771,361 B2 | 7/2014 | Hall | |
| 8,777,875 B2* | 7/2014 | Park | A61B 17/155 600/587 |
| 9,278,413 B2 | 3/2016 | Sperling | |
| 9,320,608 B2 | 4/2016 | Sperling | |
| 9,387,079 B2* | 7/2016 | Bojarski | A61F 2/30 |
| 9,414,928 B2 | 8/2016 | Sperling | |
| 9,700,420 B2* | 7/2017 | Fitz | A61F 2/3859 |
| 2004/0133276 A1* | 7/2004 | Lang | A61F 2/30756 623/14.12 |
| 2005/0113931 A1* | 5/2005 | Horber | A61F 2/4014 623/19.14 |
| 2005/0267584 A1* | 12/2005 | Burdulis, Jr. | A61F 2/38 623/20.19 |
| 2006/0095047 A1 | 5/2006 | de la Barrera | |
| 2007/0100353 A1* | 5/2007 | Chudik | A61F 2/4003 606/104 |
| 2007/0198022 A1 | 8/2007 | Lang et al. | |
| 2008/0269906 A1* | 10/2008 | Iannotti | A61B 90/36 623/19.11 |
| 2009/0226068 A1* | 9/2009 | Fitz | A61F 2/3872 382/131 |
| 2009/0270868 A1 | 10/2009 | Park et al. | |
| 2011/0029091 A1* | 2/2011 | Bojarski | A61F 2/30942 623/20.32 |
| 2011/0029093 A1* | 2/2011 | Bojarski | A61F 2/3859 623/20.35 |
| 2011/0305379 A1* | 12/2011 | Mahfouz | A61B 8/4245 382/131 |
| 2012/0078258 A1* | 3/2012 | Lo | A61B 17/1778 606/87 |
| 2012/0277880 A1 | 11/2012 | Winslow et al. | |
| 2014/0257508 A1* | 9/2014 | Bojarski | A61F 2/30942 623/20.35 |
| 2015/0032215 A1* | 1/2015 | Slamin | A61F 2/30942 623/20.21 |
| 2015/0342739 A1* | 12/2015 | Mahfouz | G06F 17/18 623/20.35 |
| 2017/0367834 A1* | 12/2017 | Fitz | A61F 2/4081 |

FOREIGN PATENT DOCUMENTS

| | | |
|---|---|---|
| WO | 2007092841 | 8/2007 |
| WO | 2012030794 A1 | 3/2012 |
| WO | 2014035991 A1 | 3/2014 |

OTHER PUBLICATIONS

Friedman, et al., The Use of Computerized Tomography in the Measurement of Glenoid Version, Journal of Bone and Joint Surgery, 1992, 74-A(7):1032-1037.

Habermeyer, et al., Three-Dimensional Glenoid Deformity in Patients with Osteoarthritis: A Radiographic Analysis, Journal of Bone & Joint Surgery Am., 2006, 88:1301-1307.

Hertel, et al., Geometry of the Proximal Humerus and Implications for Prosthetic Design, J. Shoulder Elbow Surg., 2002, 11:331-338.

Hoenecke Jr., et al., Optimizing Glenoid Component Position Using Three-Dimensional Computed Tomography Reconstruction, J. Shoulder Elbow Surg., 2008, 17:637-641.

Hoenecke Jr., et al., Accuracy of CT-Based Measurements of Glenoid Version for Total Shoulder Arthroplasty, J. Shoulder Elbow Surg., 2010, 19:166-171.

Jones, Addressing Glenoid Erosion in Anatomic Total Shoulder Arthroplasty, Bulletin of the Hospital for Joint Diseases, 2013, 71 (Suppl 2):S46-S50.

Kandemir, et al., The Relationship Between the Orientation of the Glenoid and Tears of the Rotator Cuff, Journal of Bone and Joint Surgery (Br), 2006, 88-B:1105-1109.

Lewis, et al., Location of the Optimized Centerline of the Glenoid Vault: A Comparison of Two Operative Techniques with Use of Three-Dimensional Computer Modeling, Journal of Bone and Joint Surgery Am., 2010, 92:1188-1194.

Matsumura, et al., Computed Tomography Meaurement of Glenoid Vault Version as an Alternative Measuring Method for Glenoid Version, Journal of Orthopaedic Surgery and Research, 2014, 9:17-23.

Computer Assessment of Scapula Cortical and Cancellous Bone Removal When Correcting a Posterior Defect Using Three Different Glenoid Prosthesis Designs [Results of Computer Analysis Accepted for Presentation at 2013 Orthopaedic Research Society], Copyright 2013 Exactech, Inc., 4 pages.

Rispoli, et al., Projection of the Glenoid Center Point Within the Glenoid Vault, Clin. Orthop. Relat. Res., 2008, 466:573-578.

Sabesan, et al., Guidelines for the Selection of Optimal Glenoid Augment Size for Moderate to Severe Glenohumeral Osteoarthritis, Journal of Shoulder and Elbow Surgery, Article in Press 2013, pp. 1-8.

PCT International Search Report and Written Opinion, PCT/US2011/49686, dated Dec. 28, 2011.

Biomet Orthopedics, Bio-Modular Choice Shoulder System, Surgical Technique, Standard and Mini Stem, Brochure, Rev. Nov. 15, 2008.

Biomet Orthopedics, Comprehensive Total Shoulder System, Brochure, Rev. Dec. 15, 2011.

Biomet Orthopedics, Comprehensive Total Shoulder System Featuring Comprehensive Access Glenoid Instrumentation. Surgical Technique, Brochure, Rev. Nov. 30, 2012.

Smith & Nephew, Inc., Cofield Total Shoulder System, Surgical Technique, Brochure, May 1997.

Depuy Orthopaedics Inc., Global Steptech, Anchor Peg Glenoid, Shoulder Arthroplasty System, Hospital Value Dossier, Brochure, Copyright DePuy Otrthopaedics, Inc. 2011.

Exactech, Equinoxe Operative Technique Addendum, Posterior Augment Glenoid, Brochure, Copyright 2011 Exactech, Inc.

PCT International Search Report and Written Opinion, PCT/US2015/034211, dated Sep. 3, 2015.

Hiroshi Tumura, Ninth Chapter Preoperative Plan 3) Preoperative Measurement, Total Knee Arthroplasty—Basic and Clinical—Japan, Bunkodo Co., Nov. 29, 2007, First Edition, 3rd Impression, pp. 188-191.

Kazuo Fujiwara, Nobuhiro Abe, Preparation for Operation, The Importance of the Preoperative Plan, Mainly About Imaging, Total Knee Arthroplasty (TKA), Japan, Kato-Bunmeisya Co., Sep. 10, 2007, First Edition, 2nd Impression, pp. 52-58.

Japanese Office Action for application 2018-228388, dated Mar. 19, 2019, 8 pages, with associate translation.

Australian Examination Report No. 1 for application 2015275082, dated Mar. 7, 2019, 4 pages.

Japanese Office Action, dated Feb. 5, 2019, 5 pages, with associate translation.

\* cited by examiner

METHOD FOR OPTIMIZATION OF JOINT ARTHROPLASTY COMPONENT DESIGN

CROSS-REFERENCES TO RELATED APPLICATIONS

This is a divisional application of U.S. patent application Ser. No. 15/429,037, filed Feb. 9, 2017, which is a continuation application of U.S. patent application Ser. No. 15/063,021, filed Mar. 7, 2016, which is a continuation application of U.S. patent application Ser. No. 13/818,738, filed Feb. 25, 2013, now U.S. Pat. No. 9,278,413, which is a 371 national stage entry of PCT International Application PCT/US2011/49686 filed Aug. 30, 2011, which claims the benefit of U.S. Provisional Patent Application 61/379,222, filed Sep. 1, 2010 and U.S. Provisional Patent Application 61/379,634 filed Sep. 2, 2010, which are incorporated herein by reference for all purposes.

STATEMENT REGARDING FEDERALLY SPONSORED RESEARCH

Not Applicable.

BACKGROUND OF THE INVENTION

1. Field of the Invention

The invention relates to a method for the optimization of joint arthroplasty component design, and more particularly to a method for the optimization of shoulder arthroplasty component design through the use of computed tomography scan data from arthritic shoulders.

2. Description of the Related Art

Various prostheses for the replacement of the shoulder joint are known. In one example shoulder prosthesis, the upper portion of the humerus is replaced by a humeral component including (i) a stem that extends into a bore formed within the humerus and (ii) a generally hemispherical head portion that is connected to the stem. The hemispherical head of the humeral component articulates with a complementary concave section of a glenoid component mounted within the glenoid cavity of the scapula. This type of shoulder prosthesis may be called a "primary" or "total" prosthesis. In another example shoulder prosthesis, often called a "reverse" or "inverted" prosthesis, the glenoid component includes a convex section that articulates with a complementary concave section of the head of the humeral component.

One alternative to total shoulder replacement is referred to as shoulder hemiarthroplasty. In one version of this procedure, the humeral head is replaced with a generally hemispherical head that may or may not include a connected stem. The glenoid cavity of the scapula is not replaced with a glenoid component, but may be refinished in a way that gives it a smooth surface and a shape which matches the generally hemispherical replacement head. Another version of this procedure can use a glenoid component with resurfacing of the humeral head.

Several deficiencies have been found in currently available shoulder arthroplasty systems including glenoid sizes (primary and reverse) and humeral sizes that are not based on the anatomic distribution. In addition, the advent of reverse arthroplasty for the treatment of proximal humerus fractures has also changed the requirements for an appropriate fracture stem. Specific design features are necessary to make the fracture stem appropriate for hemiarthroplasty and reverse arthroplasty use. Although resurfacing of the humerus has become popular, the designs are not based on an anatomic distribution. The instrumentation that is currently available is inadequate and may lead to significant malposition in version and inclination.

Prior magnetic resonance imaging and cadaveric studies of glenohumeral anatomy have been performed on shoulders without arthritis (Iannotti et al., "The normal glenohumeral relationships. An anatomical study of one hundred and forty shoulders", *J Bone Joint Surg Am.* 1992; 74:491-500; Hertel et al., "Geometry of the proximal humerus and implications for prosthetic design", *J Shoulder Elbow Surg.*, July/August 2002, pp. 331-338; and Boileau et al., "The Three-Dimensional Geometry Of The Proximal Humerus—Implications For Surgical Technique And Prosthetic Design", *J Bone Joint Surg* [Br], 1997; 79-B:857-865). However, in reality, shoulder arthroplasty is not performed on normal shoulders. Shoulder arthroplasty is performed in patients with arthritis in the setting of cartilage loss and usually associated bone loss. In order to make properly sized implants that will accommodate patients with arthritis, it is important to understand the anatomy of these patients.

Typically, the designing surgeon has used a system with three glenoid sizes. In one study, it was determined that the distribution of glenoid components used in total shoulder arthroplasty was as follows: 4% large, 40% medium, and 56% small. One can see that based on component use, the sizing of these implants is not optimal. If glenoid component sizes are not optimal, there may be issues related to perforation of the glenoid by fasteners used in attaching the glenoid component to the scapula. In addition, certain components may be too large for smaller patients resulting in component overhang and potentially leading to violation of important neurovascular structures. Thus, it could be hypothesized that the preference for small glenoid components may result from the desire to avoid glenoid perforation and/or avoid component overhang. However, larger glenoid components can lead to a better fitting prosthesis and greater stability.

Thus, there exists a need for a method for the optimization of joint arthroplasty component design, and in particular, there exists a need for a method for the optimization of shoulder arthroplasty component design.

SUMMARY OF THE INVENTION

The present invention addresses the foregoing needs by providing methods for the optimization of joint arthroplasty component design.

In one aspect, the invention provides a method for manufacturing a prosthetic component for replacing a part of a bone of a joint in a subject. The method comprises: (a) obtaining an axial image of the bone of the joint; (b) orienting on the image a reference angle from a body of the bone to create a neutral face plate line that extends from a first border of the bone to an opposite second border of the bone; (c) measuring a length of the neutral face plate line; and (d) manufacturing the prosthetic component to include a base surface and an opposed articular surface wherein a width of the base surface is a predetermined percentage of the length of the neutral face plate line. For example, the width of the base surface may be the same or less than the length of the neutral face plate line.

In another aspect, the invention provides a method for manufacturing a prosthetic component for replacing a part of a bone of a joint in a subject. The method comprises: (a) obtaining an axial image of the bone of the joint; (b) orienting on the image a reference angle from a body of the bone to create a neutral face plate line that extends from a first border of the bone to an opposite second border of the bone; (c) orienting on the image a first reference line perpendicular to the neutral face plate line and extending over the bone in the image; (d) measuring a first reference length of the first reference line from the neutral face plate line perpendicular to a depth of a cavity in the bone; and (e) manufacturing the prosthetic component to include an articular section and a projection extending away from the articular section wherein a length of the projection is a predetermined percentage of the first reference length. For example, the length of the projection is typically less than the first reference length.

In another aspect, the invention provides a method for manufacturing a glenoid component for replacing a part of a scapula of a shoulder joint in a subject, the method comprises: (a) obtaining a sagittal image of the glenoid of the scapula; (b) orienting on the image a first reference line that extends perpendicularly from an inferior border of the glenoid image over the scapula in the image; (c) orienting on the image a second reference line that perpendicularly intersects the first reference line and that extends from a first border of the scapula to an opposite second border of the scapula; (d) measuring a length of the second reference line; and (e) manufacturing the glenoid component to have a width that is a predetermined percentage of the length of the second reference line. For example, the width of the glenoid component may be the same or less than the length of the second reference line.

In another aspect, the invention provides a method for manufacturing a prosthetic component for replacing a part of a bone of a joint in a subject. The method comprises: (a) obtaining a coronal image of the bone of the joint; (b) orienting on the image a first reference line that extends from a first border of a head of the bone to an opposite second border of the head of the bone; (c) orienting on the image a 90 degree reference angle from an inferior position of the first reference line to create a second reference line that extends over the image of the bone; (d) orienting on the image a third reference line that extends over the image of the bone from the second reference line to a superior aspect of a tuberosity of the bone; (e) measuring a length of the third reference line; and (f) manufacturing the prosthetic component to include a protruding section wherein a length of the protruding section is a predetermined percentage of the length of the reference line.

In another aspect, the invention provides a method for manufacturing a prosthetic component for replacing a part of a bone of a joint in a subject. The method comprises: (a) obtaining a coronal image of the bone of the joint; (b) orienting on the image a first reference line that extends from a first border of a head of the bone to an opposite second border of the head of the bone; (c) orienting on the image a ninety degree reference angle from an inferior position of the first reference line to create a second reference line that extends over the image of the bone; (d) orienting on the image a third reference line that extends over the image of the bone from the second reference line to a superior border of a tuberosity of the bone; (e) orienting on the image a fourth reference line that extends over the image of the bone from the third reference line to a side border of the tuberosity of the bone; (f) measuring a length of the fourth reference line; and (g) manufacturing the prosthetic component to include a protruding section wherein a diameter of the protruding section is a predetermined percentage of the length of the fourth reference line.

In another aspect, the invention provides a method for manufacturing a prosthetic component for replacing a part of a bone of a joint in a subject. In the method, the prosthetic component is formed to include a base surface and an opposed articular surface wherein a width of the base surface is a predetermined percentage of a length of a neutral face plate line. The length of the neutral face plate line used by the manufacturer in forming the prosthetic component has been determined by (i) obtaining an image of the bone of the joint, (ii) orienting on the image a reference angle from a body of the bone to create the neutral face plate line, wherein the neutral face plate line extends from a first border of the bone to an opposite second border of the bone, and (iii) measuring the length of the neutral face plate line. The predetermined percentage of the length of a neutral face plate line used by the manufacturer in forming the prosthetic component can be 100% or less, 90%-99%, or 80%-99%. The predetermined percentage can be greater than, equal to, or less than 100%, and can take into account a range of data values observed when analyzing a number of images for the measurement of interest. For example, the predetermined percentage can be selected to include any number of standard deviations above a mean of the collected measurement data. The joint can be arthritic. In one form, at least a section of the base surface of the prosthetic component is flat. For example, the base surface of the prosthetic component can be flat around a central post that extends away from the base surface of the prosthetic component. The neutral face plate line can correspond to a width of a flat neutral face plate formed by removing a portion of the bone during arthroplasty. In one version of the method, the bone is the scapula, and the joint is the shoulder. The prosthetic component can be a glenoid component. The image can be a computed tomography scan slice, and the reference angle can be 90 degrees. In one version of the method, the neutral face plate line is a straight line positioned completely within a perimeter of the image of the bone from the first border of the bone to the second border of the bone. At least a section of the straight line is spaced from a portion of the perimeter of the image of the bone, and the portion of the perimeter of the image of the bone represents a natural articular surface of the bone.

In another aspect, the invention provides a method for manufacturing a prosthetic component for replacing a part of a bone of a joint in a subject. In the method, the prosthetic component is formed to include an articular section and a projection extending away from the articular section wherein a length of the projection is a predetermined percentage of a first reference length. The first reference length used by the manufacturer in forming the prosthetic component has been determined by (i) obtaining an image of the bone of the joint, (ii) orienting on the image a reference angle from a body of the bone to create a neutral face plate line that extends from a first border of the bone to an opposite second border of the bone, (iii) orienting on the image the first reference line, the first reference line being perpendicular to the neutral face plate line and extending over the bone in the image, (iv) measuring the first reference length of the first reference line from the neutral face plate line perpendicular to a depth of a cavity in the bone. The predetermined percentage of the first reference length can be 100% or less, 90%-99%, or 80%-99%. The predetermined percentage can be greater than, equal to, or less than 100%, and can take into account a range of data values observed when analyzing a number of images for the measurement of interest. For example, the predetermined percentage can be selected to include any number of standard deviations above a mean of the collected measurement data. The projection can be a post. In one version of the method, the prosthetic component is formed such that the length of the projection is a predetermined percentage of a second reference length. The second reference length used by the manufacturer in forming the prosthetic component has been determined by (i) orienting on the image a second reference line parallel to the first reference line and extending over the bone in the image, (ii) measuring the second reference length of the second reference line from the neutral face plate line to the depth of a cavity in the bone. In one version of the method, the bone is the scapula, and the joint is an arthritic shoulder, and the prosthetic component is a glenoid component. The image can be a computed tomography scan slice. In one version of the method, the neutral face plate line is a straight line positioned completely within a perimeter of the image of the bone from the first border of the bone to the second border of the bone. At least a section of the straight line is spaced from a portion of the perimeter of the image of the bone, and the portion of the perimeter of the image of the bone represents a natural articular surface of the bone.

In another aspect, the invention provides a method for manufacturing a glenoid component for replacing a part of a scapula of a shoulder joint in a subject. In the method, the glenoid component is formed to have a width that is a predetermined percentage of a length of a second reference line. The length of the second reference line used by the manufacturer in forming the prosthetic component has been determined by (i) obtaining an image of the glenoid of the scapula, (ii) orienting on the image a first reference line that extends perpendicularly from an inferior border of the glenoid image over the scapula in the image, (ii) orienting on the image the second reference line, the second reference line perpendicularly intersecting the first reference line and extending from a first border of the scapula to an opposite second border of the scapula, and (iii) measuring the length of the second reference line. The predetermined percentage of the length of the second reference line can be 100% or less, 90%-99%, or 80%-99%. The predetermined percentage can be greater than, equal to, or less than 100%, and can take into account a range of data values observed when analyzing a number of images for the measurement of interest. For example, the predetermined percentage can be selected to include any number of standard deviations above a mean of the collected measurement data. The second reference line intersects the first reference line at about 10 to 18 millimeters above the inferior border of the glenoid image. The second reference line preferably intersects the first reference line at about 14 millimeters above the inferior border of the glenoid image. The image can be a computed tomography scan slice.

In another aspect, the invention provides a method for manufacturing a prosthetic component for replacing a part of a bone of a joint in a subject. In the method, the prosthetic component is formed to include a protruding section wherein a first length of the protruding section is a predetermined percentage of a length of the third reference line. The length of the third reference line used by the manufacturer in forming the prosthetic component has been determined by (i) obtaining an image of the bone of the joint, (ii) orienting on the image a first reference line that extends from a first border of a head of the bone to an opposite second border of the head of the bone, (iii) orienting on the image a 90 degree reference angle from an inferior position of the first reference line to create a second reference line that extends over the image of the bone, (iv) orienting on the image the third reference line, the third reference line extending over the image of the bone from the second reference line to a superior aspect of a tuberosity of the bone, and (v) measuring the length of the third reference line. In one version of the method, the prosthetic component is formed such that a second length of the projection is a predetermined percentage of a fourth reference length wherein the second length of the projection is perpendicular to the first length of the projection. The fourth reference length used by the manufacturer in forming the prosthetic component has been determined by (i) orienting on the image a fourth reference line perpendicular to the third reference line and extending over the bone in the image from the third reference line to a perimeter of the bone in the image, and (ii) measuring the fourth reference line to determine the fourth reference length. In one version of the method, the bone is the humerus, the joint is the shoulder, the length of the third reference line is a superior-inferior length of a greater tuberosity of the humerus, and the fourth reference length is a medial-lateral length of the greater tuberosity of the humerus. In one version of the method, the joint has been fractured, and the protruding section includes a plurality of fins for immobilizing fracture fragments.

In another aspect, the invention provides a method for manufacturing a prosthetic component for replacing a part of a bone of a joint in a subject. In the method, the prosthetic component is formed to include a head and a stem connected to the head. The head has a longitudinal head axis and the stem has a longitudinal stem axis. The head axis and the stem axis are angled to create an inclination angle between the head axis and the stem axis. The inclination angle used by the manufacturer in forming the prosthetic component has been determined by (i) obtaining an image of the bone of the joint, (ii) orienting on the image a first reference line that extends from a first border of a head of the bone to an opposite second border of the head of the bone, (iii) orienting on the image a 90 degree reference angle from an inferior position of the first reference line to create a second reference line that extends over the image of the bone, (iv) orienting on the image the third reference line, the third reference line extending over the image of the bone from the second reference line to a superior aspect of a tuberosity of the bone, and (v) measuring an angle between the first reference line and the third reference line, wherein the angle is equal to the inclination angle. In one version of the method, the bone is the humerus, and the joint is an arthritic shoulder. The image can be a computed tomography scan slice.

In another aspect, the invention provides a method for manufacturing a prosthetic component for replacing a part of a bone of a joint in a subject. In the method, the prosthetic component is formed to include an articular head and an opposed base surface. The head has a longitudinal head axis, and the head axis and the base surface are angled to create an inclination angle between the head axis and the base surface. The inclination angle used by the manufacturer in forming the prosthetic component has been determined by (i) obtaining an image of the bone of the joint, (ii) orienting on the image a first reference line that extends from a first border of a head of the bone to an opposite second border of the head of the bone, (iii) orienting on the image a 90 degree reference angle from an inferior position of the first reference line to create a second reference line that extends over the image of the bone, (iv) orienting on the image the third reference line, the third reference line extending over the image of the bone from the second reference line to a superior aspect of a tuberosity of the bone, and (v) measuring an angle between the first reference line and the third reference line, the angle being equal to the inclination angle. In one version of the method, the bone is the humerus, and the joint is an arthritic shoulder. The image can be a computed tomography scan slice.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
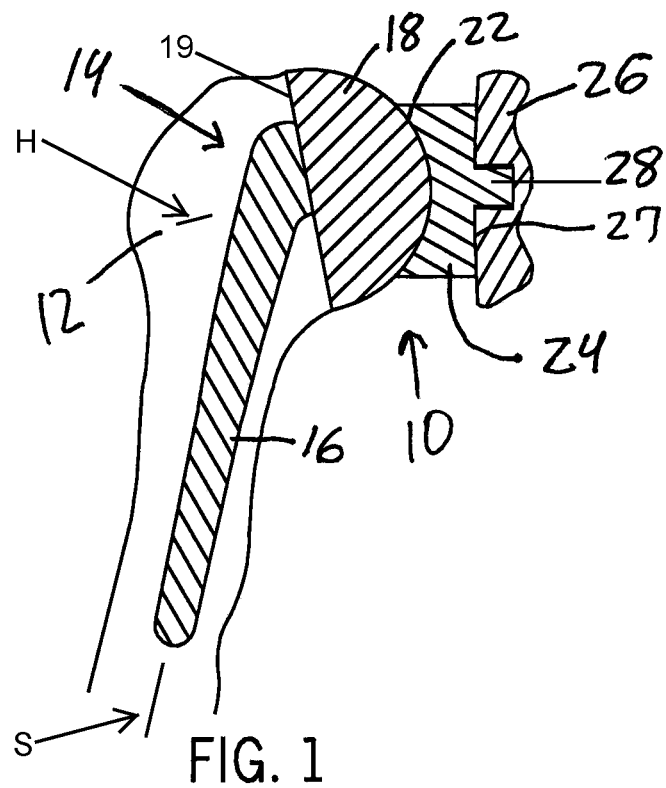
FIG. 1 is a cross-sectional view of one embodiment of a shoulder prosthesis suitable for use in the invention.

Looking first at FIG. 1, there is shown one example embodiment of a shoulder prosthesis 10 suitable for use in the invention. The upper portion of the humerus 12 is replaced by a humeral component 14 including a stem 16 that extends into a bore formed within the humerus 12. Typically, the stem 16 is fixed within the bore formed within the humerus 12. The stem 16 has a longitudinal stem axis S. A generally hemispherical head 18 is connected to the stem 16. The stem 16 can be monolithic with the head 18, or the stem 16 and the head 18 can formed as separate parts. The hemispherical head 18 has a base surface 19 and a longitudinal head axis H. The hemispherical head 18 of the humeral component 14 articulates with a complementary concave section 22 of a glenoid component 24 that is fixed within the glenoid cavity of the scapula 26 (shown cutaway) using cemented or uncemented posts 28. The glenoid component 24 includes a base surface 27 opposite the concave section 22 that serves as an articular surface of the glenoid component 24.

Proper design and selection of the hemispherical head 18 and the glenoid component 24 can be achieved using the method of the invention. In one non-limiting example method of the invention, eleven measurements are obtained using CT slices. The eleven measurements are as follows: (1) glenoid version; (2) anterior-posterior (AP) diameter at the articular surface; (3) anterior-posterior width at a neutral face plate; (4) depth of the glenoid vault from a neutral face plate; (5) depth of the glenoid vault from a neutral face plate with a diameter of the center post (an example center post diameter being five millimeters); (6) superior-inferior glenoid height; (7) determination of the anterior-posterior width fourteen millimeters from the inferior border of the glenoid; (8) humeral head diameter; (9) humeral head thickness; (10) greater tuberosity length of the humerus; (11) greater tuberosity width of the humerus; and (12) humeral inclination.

Various combinations of these measurements are used for manufacturing a prosthetic component for replacing a part of a bone of a joint in a subject (e.g., mammal). The prosthetic component may be formed from, for example: (i) a metal or metal alloy such as a titanium alloy (e.g., titanium-6-aluminum-4-vanadium), a cobalt alloy, a stainless steel alloy, or tantalum; (ii) a nonresorbable ceramic such as aluminum oxide or zirconia; (iii) a nonresorbable polymeric material such as polyethylene; or (iv) a nonresorbable composite material such as a carbon fiber-reinforced polymers (e.g., polysulfone). The prosthetic component can be manufactured by machining an article formed from these materials, or by molding these materials in a suitable mold.

Examples

The following Examples have been presented in order to further illustrate the invention and are not intended to limit the invention in any way.

1. Glenoid Version

Using an axial 2D CT scan of a human shoulder, the mid point of the glenoid was determined. A first line was then drawn through the midpoint and parallel to the scapular body. The first line intersects a second line drawn parallel to the joint surface. The glenoid version was the angle between the first line and the second line, and was recorded in degrees.

2. Anterior-Posterior (AP) Width at the Articular Surface

Using an axial 2D CT scan of a human shoulder, the diameter (AP width) was measured at the mid-point of the glenoid in millimeters.

3. Anterior-Posterior (AP) Width at a Neutral Face Plate

Figure 2:
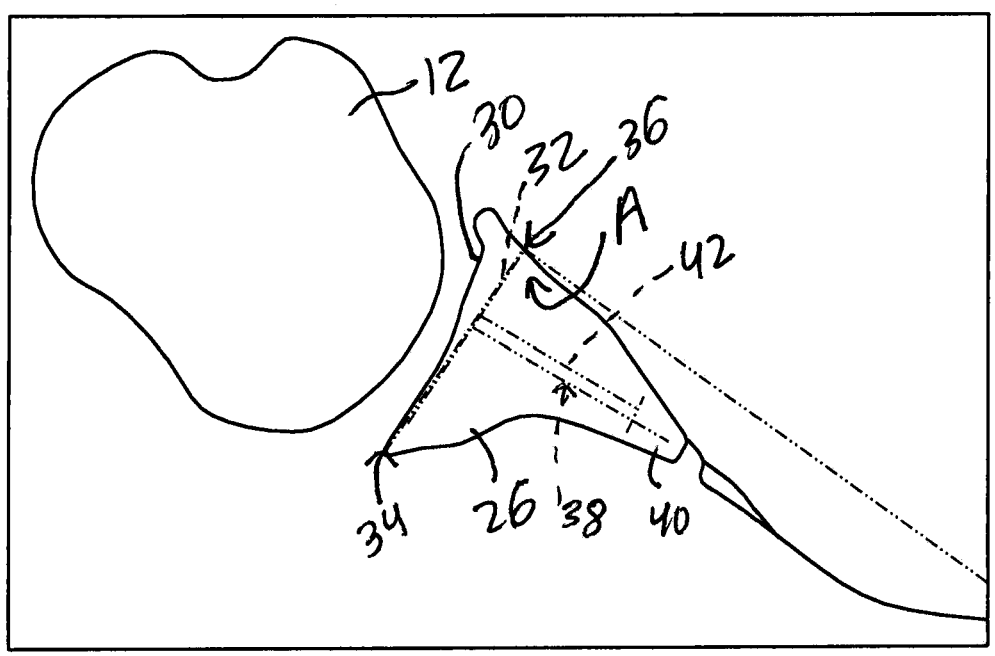
FIG. 2 shows a tracing of a computed tomography (CT) axial two-dimensional (2D) CT slice of the scapula and humerus with measurement lines according to the invention shown in broken lines.

Looking at FIG. 2, an axial 2D CT scan of a human shoulder was obtained and a 90 degree angle A (shown in broken lines) was oriented from the scapular body 26 and then placed on the glenoid 30 to create a neutral face plate 32 (shown in broken lines) that runs from one side border 34 to the other side border 36 of the glenoid 30. This width was then measured in millimeters. This measurement is important to determine the true AP width of the glenoid after creating a flat neutral face plate by removing bone during arthroplasty. This is what occurs at surgery according to the method of the invention, yet this measurement has never been previously described. Prior measurements have been made of the articular surface only of the glenoid. This explains why many glenoid component sizes are too large. The measurement at a neutral faceplate is usually several millimeters less than the measurement at the articular surface due to reaming or removing glenoid bone to make the surface flat to place the glenoid component 24.

When manufacturing a glenoid component, a manufacturer can be supplied with the length of the neutral face plate 32 which provides a true AP width of the glenoid after creating a flat neutral face plate by removing bone during arthroplasty. A predetermined percentage of the length of the neutral face plate 32 can be used to machine or mold the glenoid component to have a selected width for the base surface 27 (see FIG. 1).

4. Depth of the Glenoid Vault from a Neutral Face Plate

Still looking at FIG. 2, a line 38 (shown in broken lines) was started at the neutral face plate 32 and was drawn medially to determine the depth of the glenoid vault 40. Previous reports have mentioned only the depth from the articular surface which overstates the depth of the glenoid. This explains why many central posts or peripheral pegs of glenoid components that are currently in the market are too long and perforate the glenoid. Prior designs have not been designed based on patients with arthritis and associated bone loss who have undergone shoulder arthroplasty.

When manufacturing a glenoid component, a manufacturer can be supplied with the length of the line 38. A predetermined percentage of the length of the line 38 can be used to machine or mold the glenoid component to have a selected longitudinal length for the post 28 (see FIG. 1).

5. Depth of the Glenoid Vault from a Neutral Face Plate with a Diameter of 5 Millimeters Still looking at FIG. 2, a five millimeter line 42 (shown in broken lines) was placed within the vault parallel to the line 38. This will show one the depth of the glenoid vault that one can drill back to a five millimeter diameter. This allows accurate determination of the safe length for a central post or screw. Other post diameters are allowed in the design, five millimeters is used only as an example.

When manufacturing a glenoid component, a manufacturer can be supplied with the length of the line 42. A predetermined percentage of the length of the line 42 can be used to machine or mold the glenoid component to have a selected length for the post 28 (see FIG. 1).

6. Superior-Inferior Glenoid Length

The height of the glenoid was measured in millimeters.

Figure 3:
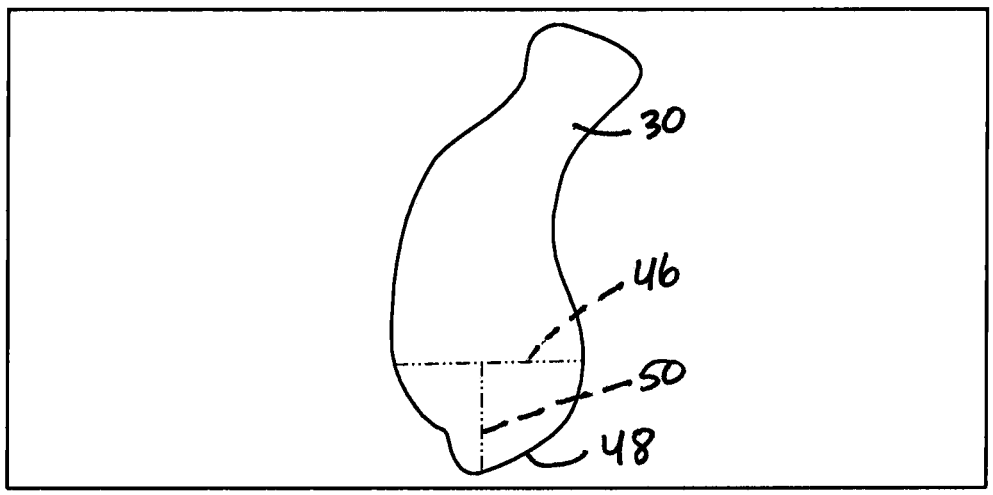
FIG. 3 shows a tracing of a 2D CT sagittal slice of the scapula with measurement lines according to the invention shown in broken lines.

7. Determination of the AP Width Fourteen Millimeters from the Inferior Border of the Glenoid Turning to FIG. 3, a 2D CT scan of a human shoulder was obtained and on the sagittal cut, an anterior-posterior width on line 46 (shown in broken lines) was measured. Line 46 was perpendicular to and fourteen millimeters up line 50 (shown in broken lines) from the inferior border 48 of the glenoid 30. This measures the anterior-posterior width of the glenoid fourteen millimeters above the inferior rim of the glenoid. This allows determination of the appropriate width of a glenoid base plate for reverse arthroplasty.

When manufacturing a glenoid component, a manufacturer can be supplied with the length of the line 46. A predetermined percentage of the length of the line 46 can be used to machine or mold the glenoid component to have a selected width for the base surface 27 (see FIG. 1).

8. Humeral Head Diameter and 9. Humeral Head Thickness

Figure 4:
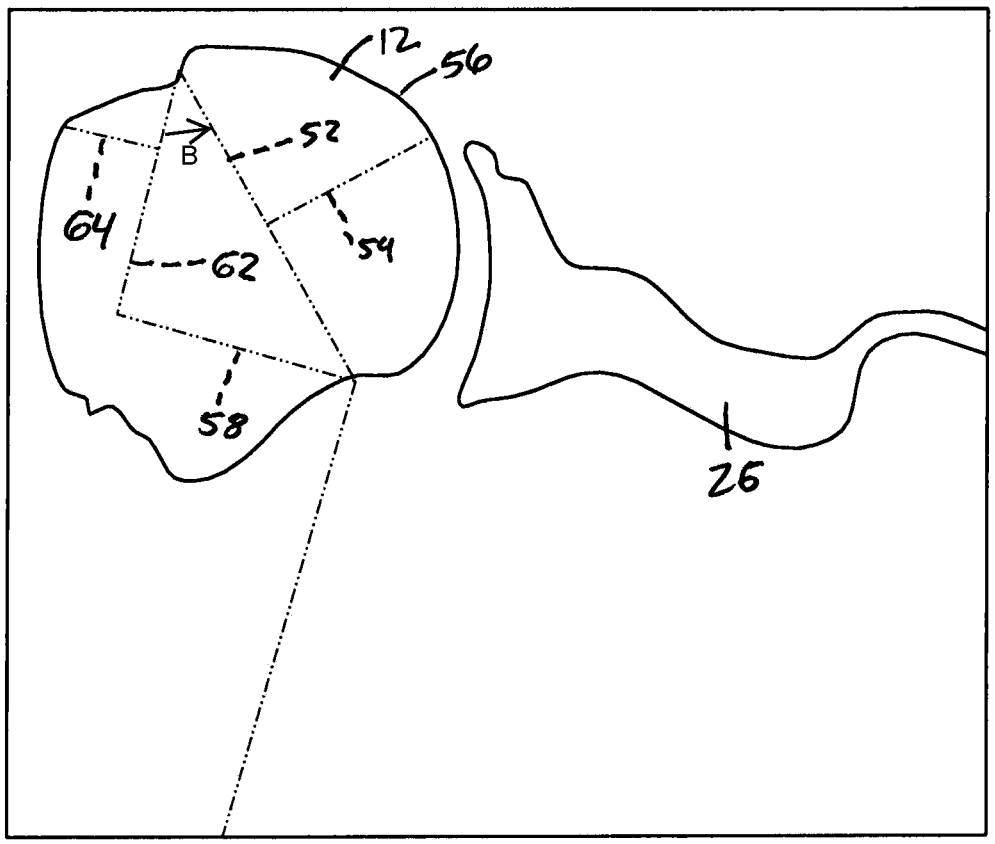
FIG. 4 shows a tracing of a CT 2D coronal slice of the scapula and humerus with measurement lines according to the invention shown in broken lines.

Turning to FIG. 4, a 2D CT scan of a human shoulder was obtained and on the coronal slice the diameter of the humeral head was measured in millimeters at line 52 (shown in broken lines). A line 54 (shown in broken lines) was then drawn perpendicular from line 52 to the surface 56 of the humeral head. The length of line 54 (here measured in millimeters) gives one the thickness of the humeral head.

10. Greater Tuberosity Length and 11. Greater Tuberosity Width

A 90 degree line 58 (shown in broken lines) was taken off the most inferior aspect of the humeral head cut. A line 62 (shown in broken lines) was then placed from the superior aspect of the greater tuberosity (intersection with the superior end point of line 52) to intersect this line 58. This line 62 shows the true distance of the greater tuberosity in length (superior-inferior). Next a line 64 (shown in broken lines) was taken 90 degrees to this line 62 to show the maximum diameter of the greater tuberosity. This line 64 shows the true distance of the greater tuberosity in width (medial-lateral). This facilitates designing a humeral component that maximizes tuberosity healing as well as anatomic component shape. This data also facilitates the design of different size humeral components specifically for fracture cases to improve tuberosity healing. This would include different size "fins" or other components to accommodate and secure fracture fragments based on the size of the patient.

12. Measurement of Humeral Inclination

On FIG. 4, taking the angle B between lines 52 and 62 in degrees and adding 90° defines the inclination angle of the humeral head in degrees (i.e., angle B in degrees+90°=the inclination of the humeral head). This measurement can determine the true range of inclination necessary for humeral component design.

When manufacturing a humeral component, a manufacturer can be supplied with the inclination angle of the humeral head. The inclination angle of the humeral head can be used to machine or mold the humeral component to have a selected angle, or a selected range of angles (for adjustable humeral inclination) between the longitudinal head axis H (see FIG. 1) and the longitudinal stem axis S (see FIG. 1) or the longitudinal head axis H and the base surface 19 (see FIG. 1).

Results

Using the measurement technique of Examples 1-12, a review of 800 patients who have undergone shoulder arthroplasty (436 total shoulder arthroplasties, 210 reverse shoulder arthroplasties, and 154 hemiarthroplasties) was completed and is shown in Table 1 below. In addition, statistical analysis revealed that when evaluating for specific anatomic ratios there were very tight confidence intervals. This can be further used to ensure proper component design as shown in Table 2.

TABLE 1

Anatomic Measurements of 800 Shoulders

| Variable | Mean | Std Dev | Median | Minimum | Maximum | 10th Pctl | 90th Pctl |
| --- | --- | --- | --- | --- | --- | --- | --- |
| 1. Glenoid version (degrees) | 10.66 | 9.68 | 10.00 | −27.00 | 49.00 | 0.00 | 24.00 |
| 2. AP width at articular surface (mm) | 28.71 | 4.32 | 28.50 | 12.40 | 41.20 | 23.30 | 34.20 |
| 3. AP width at a neutral faceplate (mm) | 24.59 | 3.83 | 24.70 | 12.00 | 36.90 | 19.80 | 29.30 |
| 4. Vault depth from a neutral face plate (mm) | 21.79 | 4.30 | 22.00 | 6.10 | 37.00 | 16.30 | 27.20 |
| 5. Vault depth to a 5 mm diameter (mm) | 16.07 | 4.2 | 16.30 | 2.00 | 27.30 | 10.80 | 21.50 |
| 6. Superior-Inferior: Glenoid Height (mm) | 34.61 | 4.4 | 34.20 | 24.00 | 50.10 | 29.10 | 40.60 |

TABLE 1-continued

Anatomic Measurements of 800 Shoulders

| Variable | Mean | Std Dev | Median | Minimum | Maximum | 10th Pctl | 90th Pctl |
|---|---|---|---|---|---|---|---|
| 7. AP width 14 mm from inferior glenoid rim (mm) | 26.78 | 3.14 | 26.80 | 15.00 | 35.20 | 22.80 | 30.80 |
| 8. Humeral head diameter (mm) | 43.47 | 4.31 | 43.00 | 32.80 | 56.00 | 38.30 | 49.60 |
| 9. Humeral head thickness (mm) | 22.11 | 2.76 | 22.20 | 14.20 | 29.70 | 18.80 | 25.60 |
| 10. Greater tuberosity superior-inferior (mm) | 33.61 | 4.54 | 33.10 | 21.00 | 47.00 | 28.00 | 40.00 |
| 11. Greater tuberosity medial-lateral (mm) | 11.29 | 2.01 | 11.00 | 6.30 | 18.00 | 8.90 | 14.00 |
| 12. Humeral Inclination (degrees) | 129.13 | 5.72 | 129.00 | 115.00 | 145.00 | 121.00 | 137.00 |

The 10th and 90th percentile refer to the range of data.

TABLE 2

| Ratio | Overall Ratio | Overall-95% Confidence Intervals |
|---|---|---|
| Humeral head diameter/Humeral head thickness | 1.98 | 1.97, 2.00 |
| Greater tuberosity medial-lateral (width)/Greater tuberosity superior-inferior (height) | 0.337 | 0.334, 0.341 |
| AP width at a neutral faceplate/Vault depth from a neutral faceplate | 1.16 | 1.14, 1.18 |

Thus, the invention provides a method for the optimization of shoulder arthroplasty component design. Use of this method and the data that it provides gives unique insight into the number, size and shape of glenoid components for total shoulder arthroplasty and reverse arthroplasty as well as humeral heads for shoulder arthroplasty and resurfacing arthroplasty. This method also provides valuable information for the optimal design, shape, and size of the proximal humeral body for a fracture stem to maximize tuberosity healing and humeral component design for hemiarthroplasty/total shoulder arthroplasty. In the course of new product development, this method is a valuable resource that can be used to radiographically evaluate each new component design to ensure optimal fit prior to component production and product launch. While the invention is described herein as a method for the optimization of shoulder arthroplasty component design, it can be used for other joints (e.g., hip, knee, elbow, foot, ankle, etc. . . . ).

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for manufacturing a prosthetic component for replacing a part of a bone of a joint in a subject, the method comprising:
forming the prosthetic component to include a proximal section and a stem connected to the proximal section, the proximal section having a longitudinal proximal section axis and the stem having a longitudinal stem axis, the proximal section axis and the stem axis being angled to create an inclination angle between the proximal section axis and the stem axis, the inclination angle having been determined by
(a) obtaining a coronal image of the bone of the joint;
(b) orienting on the image a first reference line that extends from a first border of a head of the bone to an opposite second border of the head of the bone;
(c) orienting on the image a second reference line that extends over the image of the bone from an inferior position of the first reference line to intersect a third reference line at a 90 degree angle, the third reference line being parallel to the longitudinal stem axis and extending over the image of the bone from the second reference line to a superior aspect of a tuberosity of the bone;
(d) measuring a reference angle between the first reference line and the third reference line; and
(e) determining the inclination angle from the reference angle.

2. The method of claim 1 wherein the bone is a humerus, and the joint is a shoulder.

3. The method of claim 1 wherein the image is a computed tomography scan slice.

4. The method of claim 1, wherein determining the inclination angle includes adding 90 degrees to the reference angle.

5. The method of claim 1, wherein the inclination angle ranges from greater than or equal to 115 degrees to less than or equal to 145 degrees.

6. The method of claim 5, wherein the inclination angle is 129.13±5.72 degrees.

7. The method of claim 1 wherein the proximal section comprises an articular surface.

8. The method of claim 7 wherein the articular surface is convex.

9. The method of claim 7 wherein the articular surface is concave.

* * * * *